United States Patent [19]

Unger et al.

[11] Patent Number: 5,244,460
[45] Date of Patent: Sep. 14, 1993

[54] METHOD TO FOSTER MYOCARDIAL BLOOD VESSEL GROWTH AND IMPROVE BLOOD FLOW TO THE HEART

[75] Inventors: Ellis F. Unger, Silver Spring; Stephen E. Epstein, Rockville, both of Md.

[73] Assignee: The United States of America as represented by the Secretary of the Department of Health & Human Services, Washington, D.C.

[21] Appl. No.: 799,830

[22] Filed: Nov. 27, 1991

[51] Int. Cl.⁵ .............................................. A61M 31/00
[52] U.S. Cl. ..................................................... 604/53
[58] Field of Search ................... 604/53, 890.1, 49, 50, 604/51, 52; 424/565; 514/41

[56] References Cited

U.S. PATENT DOCUMENTS

| | | |
|---|---|---|
| 4,296,100 | 10/1981 | Franco . |
| 4,778,787 | 10/1988 | Catsimpoolas et al. . |
| 4,868,113 | 9/1989 | Jaye et al. . |
| 4,911,717 | 3/1990 | Gaskill, III ............................ 623/11 |
| 5,021,044 | 6/1991 | Sharkawy ............................. 604/53 |
| 5,026,839 | 6/1991 | Moscatelli et al. . |

FOREIGN PATENT DOCUMENTS

| | | |
|---|---|---|
| 297262 | 5/1988 | European Pat. Off. . |
| WO91/13649 | 9/1991 | PCT Int'l Appl. . |

OTHER PUBLICATIONS

Lang Medical Publications, Los Angeles, Calif., Krupp et al., 1985, pp. 220–229.
"Effects of Acidic Fibroblast Growth Factor on Normal and Ischemic Myocardium", Banai et al., Circulation Research, vol. 69, No. 1, Jul. 1991, pp. 76–85.

*Primary Examiner*—David Isabella
*Attorney, Agent, or Firm*—Lowe, Price, LeBlanc & Becker

[57] ABSTRACT

A method for facilitating in a damaged heart or a heart in need of improved circulation the growth of cardiac blood vessels while reducing the risk of undesired vascularization in other areas of the body comprises:

(a) inserting a catheter into a coronary artery and providing an infusion port of said catheter accessible to the administration of coronary drug injections;

(b) injecting an effective amount into the heart of a blood vessel growth promoting peptide through said infusion port of said catheter; and (c) repeating periodically on subsequent days the step of injecting said blood vessel growth factor via said catheter, with said periodic injections being continued until improved cardiac blood flow has been obtained. The invention may be applied to a method for treating atherosclerosis of the coronary arteries, which comprise as part of the treatment steps the above method for improving cardiac blood flow via the growth of cardiac blood vessels.

13 Claims, 2 Drawing Sheets

METHOD TO FOSTER MYOCARDIAL BLOOD VESSEL GROWTH AND IMPROVE BLOOD FLOW TO THE HEART

TECHNICAL FIELD

The present invention relates to improvements in the treatment of diseases, and more particularly to procedures and compositions used to foster myocardial blood vessel growth and improve blood flow to the heart.

BACKGROUND ART

The seriousness and prevalence of heart disease is well known to people in the medical arts. Heart attacks represent a major cause of death, particularly in industrial countries such as the U.S. During the first months following a heart attack the overall mortality rate is about 30%, with most deaths occurring in the first 24 to 48 hours. Heart attacks, or myocardial infarction (MI) may be described as ischemic necrosis that is due to partially or completely blocked coronary arteries in the heart which starves the heart muscle for nutrients and oxygen. When the deprivation of oxygen and nutrients is severe, the tissue dies and is replaced by scar tissue which is not useful as heart muscle. The patient's heart muscle is usually weakened permanently, to some degree by such scar tissue.

The substantial narrowing or occlusion of a coronary artery may be caused by thrombus (clot), by atherosclerosis, by hemorrhage into an atherosclerotic plaque, or by spastic constriction of a coronary artery. Any one of the above mechanisms or a combination of them may cause a MI.

Treatment for patients who have suffered a myocardial infarction has largely been one of containment and stabilization. Symptomatic treatment is given. The damaged vascular or myocardial system is not rebuilt. See, for example, Krupp et al, Current Medical Diagnosis and Treatment, Lang Medical Publications, Los Angeles, Calif. (1985). Recently, "thrombolytic" therapy has advanced the treatment of MI. In the first hours after infarction, streptokinase or tissue plasminogen activator (tPa) can dissolve blood clots in coronary arteries, restoring blood flow to the heart muscle and avoiding infarction. Again, the underlying damaged myocardial vasculature is not altered by this mode of treatment.

After a MI, treatment usually consists of rest; sedation; pain killers (analgesics); oxygen; drugs to reduce the work of the heart; anticoagulants to avoid possible further clots and damage; vasodilators and diuretics to lower blood pressure; coronary vasodilators such as nitroglycerin to relax the coronary arteries and cause the blood flow to improve, inotropic agents such as digitalis to slow the heart beat; and aortic balloon counter pulsation as a circulatory assistant. Current treatment will sometimes include reopening a severe blockage by balloon catheters or similar devices (angioplasty), or use of bypass surgery. Drugs are sometimes given to prevent platelet aggregation and avoid recurrent MIs for several months following the heart attack. For this purpose $\beta$-adrenergic blocking drugs are also sometimes administered.

In order to rehabilitate patients, gradual return to work and increases in exercise are generally prescribed.

In addition to the above treatments for a MI, current practice also includes preventative measures. To remedy these blocked arteries and to avoid deprivation causing scar tissue to the heart, physicians have used mechanical methods to improve the cardiac blood flow. One method involves improving cardiac blood flow by surgically bypassing diseased vessels (coronary artery bypass surgery). This involves open heart surgery where a blood vessel is taken from some other part of the body and attached to the blocked artery both in front of the blockage and beyond of it in order to bypass the obstruction and cause the blood flow to go around the blockage.

Another method for mechanically improving cardiac blood flow by opening the existing diseased vessels is called percutaneous transluminal coronary angioplasty (PTCA). This method involves inflation of a balloon inside the blood vessel at the blockage point to crack and compress the atherosclerotic material outward, hence enlarging the diameter of the vessel. In this balloon surgery, a stent a stint (a device to keep the walls of the artery from collapsing back upon themselves) may be inserted at the blockage point.

There are serious drawbacks for each of the above procedures, and none are always satisfactory. A vein is usually used for the bypass. Since a vein is flatter and has thinner walls than an artery, the vein used for the bypass also tends to become blocked. The other two methods cause damage to the artery, and the healing response of the artery to this injury often causes the buildup of a type of scar tissue which itself causes significant obstruction of the vessel. This phenomenon is called "restenosis", and it occurs in 35 to 45% of cases.

Another temporary measure for treating the heart soon after a myocardial infarction is described in U.S. Pat. No. 4,296,100, issued to Franco on Oct. 20, 1981. A fibroblast growth factor (FGF), obtained from bovine pituitary glands is used to treat the heart in vivo after myocardial infarction in amounts of 10 mg to 1 gram per 100 grams of heart of the about 90% pure FGF. A series of spaced injections (different locations in the heart) are used to distribute the desired amount of FGF over the area of the heart to be treated. This direct injection into the heart or intravenous injection is preferred. However, subcutaneous, intramuscular and oral injection is also described.

These injections described by Franco collectively concern a one-time treatment immediately following a myocardial infarction (injections are given during one 24 hour period of time) This treatment is given as close to the time the heart attack as possible in order to control damage, i.e., to immediately improve circulation and thus avoid further damage to the heart. Franco neither describes nor suggests continued or multiple treatments with FGF to improve a damaged heart or to continue to improve circulation. See column 3 and column 4. The experiments of Franco showed that by using a one time treatment he was able to reduce the infarct size (area that will scar or remain premanently damaged) in the test animal to one quarter the size of the control (non-treated) hearts. Histological study did not show any significant increase in capillary areas in the hearts as a result of such treatment with FGF. The study merely showed that the damage to animal hearts was significantly less than damage to those hearts treated with the control and no FGF. See page 4, lines 11-17, for example.

The above data related to the Franco patent could not have related to the growth of blood vessels to treat a heart attack for additional reasons. This is because blood flow must be restored to the jeopardized muscle within 6 to 8 hours to save it, and blood vessels can not possibly grow that fast. Further, some reliable data has been published recently in a peer-reviewed journal which indicates that application of fibroblast growth factor in the context of infarction may actually be dentrimental to the patient. (See, for example, Banai et al.: Effects of acidic fibroblast growth factor on normal and ischemic myuocardium, Circulation Research 69, pages 76–85 (1991)).

U.S. Pat. No. 4,778,787, issued Oct. 18, 1988 to Catsimpoolas et al, relates to treating the heart with angiogenesis healing factors. Catsimpoolas does not relate to treatment with a peptide or protein growth factor. Instead, this patent relates to treatment with omentum-derived lipid fractions, for example, from cat omentum.

Catsimpoolas et al. describe systemic (and/or local) application of omentum-derived lipid fractions or the use of their bio- or organic-synthetic or purified analogs for the acceleration of vascularization, neovascularization, vascular collateralization, promotion of perfusion, and collagen formation or scarring and organization (cellular and collagenous) of myocardiac ischemic lesions. This was regarded as surprising since lipid materials are often considered to be atherosclerotic agents which cause MIs rather than preventing them. This patent relates to the accelerated repair of a heart after MI with less scarring than would be ordinarily expected.

There is no technology in existence at the present time that can foster the in vivo growth of new blood vessels in the heart, thereby improving cardiac blood flow. That is why the somewhat unsatisfactory procedures described above are still necessary to improve cardiac blood flow.

During the last six years, a number of proteins have been characterized that promote the growth of blood vessels in vitro. Despite their great promise in the treatment of cardiovascular disease, none have been successfully utilized in vivo to date. Moreover, to the present date, there has been no publication of any data directed to using any of these proteins in vivo to generate any blood vessels in mature tissue, i.e., in non-embryonic tissue.

As stated above, polypeptides, to date, have not been successively used to promote the growth of blood vessels in the heart, to regenerate vessels in a damaged or nearby area in a heart, or over a period of time to increase cardiac blood flow in a damaged area. The focus of the prior art has been upon the prevention of damage immediately following arterial blockage in the heart or brain. Moreover, there is no method in the prior art to provide these results or any directional details or discussion relating to a suitable dosage for accomplishing regeneration of new cardiac blood vessels.

Accordingly, there is an acute need in this art for a means to target agents directly to the heart in order to actually cause or promote the growth of new cardiac blood vessels in a limited desired area and improve critical blood flow to the heart. There is a pressing need in the art for the above method to treat the millions of patients suffering with atherosclerosis of the coronary arteries. Such an approach is needed that can potentially partially or completely replace blocked coronary arteries with new blood vessels without affecting the degree of vascularity in the area of the body.

SUMMARY OF THE INVENTION

It is an object of the present invention to overcome the difficulties in the prior art as set forth in the background to the invention.

It is another object of the present invention to provide a procedure or method by which peptides may be made operable in vivo to promote new cardiac blood vessel growth in mature cardiac tissue, when such peptides have only been previously characterized or shown to promote the growth of blood vessels in vitro or in embryonic tissue.

It is a further object of the present invention to provide an improved method of treating atherosclerosis of the coronary arteries by improving cardiac blood flow by treatment with peptides that promote blood vessel growth.

In accordance with this invention there is disclosed a method to facilitate in a damaged heart or a heart in need of improved circulation the growth of cardiac blood vessels while reducing the risk of undesired vascularization in other areas of the body comprising:

(a) inserting a catheter into a coronary artery and providing an infusion port of said catheter accessible to the administration of coronary drug injections;

(b) injecting an effective amount into the heart of a blood vessel growth promoting peptide through said infusion port of said catheter; and (c) repeating periodically on subsequent days the step of injecting said blood vessel growth factor via said catheter, with said periodic injections being continued until improved cardiac blood flow has been obtained.

In accordance with the invention there is also disclosed a method of treating atherosclerosis of the coronary arteries by improving cardiac blood flow via the growth of cardiac blood vessels in a mammal, while reducing the risk of undesired vascularization in other areas of the body, comprising:

(a) inserting a catheter into a coronary artery and providing an infusion port of said catheter accessible to the administration of coronary drug injections;

(b) injecting an effective amount into the heart of a blood vessel growth promoting peptide through said infusion port of said catheter; and (c) repeating periodically on subsequent days the step of injecting said blood vessel growth factor via said catheter, with said periodic injections being continued until improved cardiac blood flow has been obtained.

DESCRIPTION OF THE INVENTION

Figure 1:
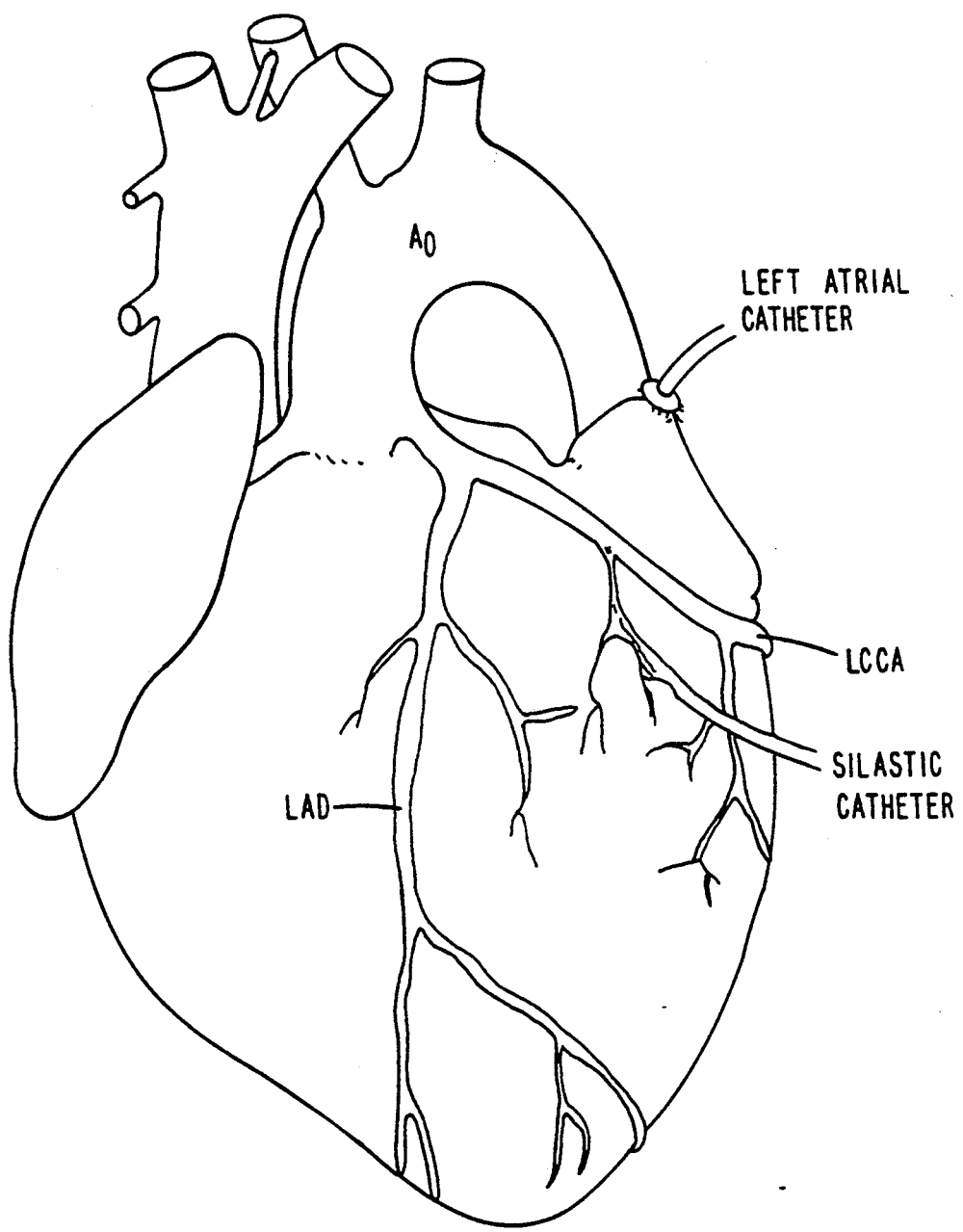
FIG. 1 is an illustration of a heart having a catheter inserted in a coronary artery through which the growth promoting peptides can be injected directly into the heart.

The phrase "repeating periodically on subsequent days," as used both above and below in describing the present invention, is defined as continuing the step of injecting the peptide into the heart at more than one time on the same day, if necessary, and on additional designated days. The is significantly more than, and substantially different than just a one-day, single- or multiple-shot treatment in or around the time of a heart attack, which one-day injections are then not repeated.

According to the present invention, the frequency of days on which the injection(s) are repeated and the duration of total time that the treatment is to be continued may be varied by routine experimentation or adapted by the patient's physician to the particular needs of a particular patient. The detailed description of the invention as set forth below describes how the frequency schedule of administration and the dosage may be adapted to the needs of a particular patient.

In accordance with this invention there is disclosed a method to facilitate in a damaged heart or a heart in need of improved circulation the growth of cardiac blood vessels while reducing the risk of undesired vascularization in other areas of the body comprising:

(a) inserting a catheter into a coronary artery and providing an infusion port of said catheter accessible to the administration of coronary drug injections;

(b) injecting an effective amount into the heart of a blood vessel growth promoting peptide through said infusion port of said catheter; and (c) repeating periodically on subsequent days the step of injecting said blood vessel growth factor via said catheter, with said periodic injections being continued until improved cardiac blood flow has been obtained.

The periods of administration of the growth factor in the method according to the invention can range from a period of a few seconds, e.g., 10 seconds, to many hours, e.g., 10 hours, contiuous administration over hours or days might also be a beneficial treatment regimen and is within the scope of the present invention.

A large number of polypeptide tissue growth factors or their bioactive fragments are known in the art which stimulate the growth of mammalian cells in vitro or in embryonic tissue. These growth factors or bioactive fragments are known to influence cellular growth, differentiation and migration. Examples of such growth factors or their bioactive fragments are epidermal growth factor, acidic fibroblast growth factor, basic fibroblast growth factor, vascular endothelial cell growth factor, and the like. Any of the peptides listed above or others that may be shown to have similar tissue growth stimulating functionality, either in vitro or in embryonic tissue, may be used in the above method.

Different alleles of the known growth factors having the activity described above are also within the scope of the present invention. Further, it is possible to produce analogs of such peptides having single or multiple amino acid substitutions, deletions, additions, or replacements. All such allelic variations, modifications, and analogs resulting in derivatives with retain the biologically active properties of native or synthetic known growth promoting peptides as described above are included within the scope of the present invention.

A particularly preferred embodiment of the present invention is a method wherein the blood vessel growth promoting peptides used for injecting into the heart to stimulate cardiac blood vessel growth are independently selected from the group consisting of vascular endothelial growth factor (VEGF) or basic fibroblast growth factor (bFGF), a growth promoting bioactive peptide fragment of vascular endothelial growth factor, a growth promoting bioactive peptide fragment of basic fibroblast growth factor, or a mixture of said peptides.

The endothelial cell growth factor may be obtained as disclosed, for example, in U.S. Pat. No. 4,868,113, issued Sep. 19, 1989, to Jaye et al, or U.S. Pat. No. applications 07/389722 (filed Aug. 4, 1989) and 07/351,117 (filed May 12, 1989), which were published as providing the priority for Australian Patent application 9056574 (published Nov. 29, 1990). Also, the basic fibroblast growth factor may be obtained as described, for example, in U.S. Pat. No., 5,026,839, issued Jun. 25, 1991, to Moscatelli et al, or Gruss et al., EP application 297262, published Jan., 4, 1989. All of the above prior art is hereby incorporated by reference with respect to their disclosures of suitable cell growth factors.

Further preferred is a method as described above wherein the periodic injections are continued for about 2 to 8 weeks and the solutions of the active ingredient are administered in a period of about 10 seconds to about 10 hours, for example, administered as a slow bolus of about 2 ml over 2 minutes followed by a 1 ml saline flush.

Also preferred is a method wherein the VEGF is administered in an amount of about 20–500 $\mu$g per injection, preferably about 25–200 $\mu$g. An even more preferred method comprises injecting about 45 $\mu$g per injection, which injection is made once per day on the days that injections are administered.

Another preferred method comprises administering bFGF in an amount of about 50–700 $\mu$g, preferably about 75–300 $\mu$g.

An even more preferred method comprises injecting 110 $\mu$g of bFGF per injection, which injection is made once per day on the days that injections are administered.

Methods for treating atherosclerosis of the coronary arteries may comprise as part of their treatment steps the above method for improving cardiac blood flow via the growth of cardiac blood vessels.

In the above embodiments of the claimed invention method, myocardial blood flow can be determined with microspheres after the placement of the catheter and prior to treatment. Advantageously, the determination can be made three days after placement of the catheter and weekly thereafter. Collateral flow can be quantified during Chromonar-induced maximum vasodilation and expressed as an ischemic/normal zone (IZ/NZ) ratio.

Accordingly, the present invention provides a method as described above and, preferably, further provides a method also comprising the step of determining the rate and sufficiency of miocardial blood flow by microspheres after the placement of the catheter and prior to treatment; and subsequently determining the rate and sufficiency of blood flow on a weekly basis during the course of treatment.

In an even further preferred embodiment of the invention regarding the monitoring of cardiac blood flow during the duration of the treatment, the step of determining the rate and sufficiency of miocardial blood flow is quantified as collateral myocardial blood flow during chromonar-induced maximum vasodilation and expressed as an ischemic/normal zone ratio represented by the formula ratio IZ/NZ.

The method for increasing cardiac blood flow according to the present invention has particular advantages since it overcomes the problems in the art related to problems of increased vascularation in undesired areas. Systemic parenterial injections or intramuscular injections would be expected to have the undesirable side effects of vascularization in undesired areas, for example, areas such as the cornea of the eye. Further, the peptides might be expected to be readily broken down by the digestive system if administered by an oral route.

Moreover, prior to the present invention the in vivo effects of tissue growth factors on mature tissue, such as those effects discussed above, were unknown and unpredictable. Surprisingly, the present inventors have discovered that the above method will promote improved cardiac circulation via the generation of new blood vessels in the heart and will avoid or minimize the undesired side effects such as increased vascularization in undesired other areas.

As noted above, the effective amounts of the peptide administered and the frequency required for injections will vary depending upon the activity of the particular peptide. Generally, the dosage may vary from a few micrograms of a peptide on a single day up to a gram or more, which may be injected as a single dose or via multiple injections on a single day. As further indicated above, a wide range of periods of administration are possible for the present invention. For example, the total dosage for the day may be administered during the period of 10 seconds to about 10 hours. Continuous administration of peptides over hours or days may be beneficial for a particular patient.

It is recommended that treatment using the above method be begun on a new patient or with a new peptide by injecting only a few micrograms of the peptide just one time per day, at first, and occasionally omitting a day or two. After two or more weeks, the progress of the patient can be checked by testing for an increase in cardiac circulation. The amount of peptide injected or the number of injections on a given day may then be varied to obtain the desired level of increase in cardiac circulation.

The peptide injected may be a single peptide or a mixture of peptides. Also, the peptide injected may be varied from day to day. Thus, the method, frequency of injections, and the peptide injected may be varied and adapted to meet the treatment needs of a particular patient.

By way of example of the invention method, disclosed below are specific experimental data relating to the growth of cardiac blood vessels in dogs which clearly prove the utility of the present process.

EXAMPLE 1

The process of the invention was used to facilitate the growth of cardiac blood vessels in dogs. General anesthesia was induced with acepromazine, thiopental sodium, and halothane. A thoracotomy was performed in the left fifth intercostal space using sterile techniques. The left circumflex coronary artery (LCX) was isolated, and the first marginal branch of the LCX was ligated 20 mm away from its origin. A silastic catheter was inserted proximal to the ligature and advanced retrogradely until the end was positioned at the takeoff of the marginal branch from the LCX (see FIG. 1). The infusion port of the catheter was secured in the subcutaneous tissues of the left lateral abdominal wall, establishing access for intracoronary drug injections. The pericardium and chest were closed in layers and the dogs were allowed to recover. Ten days after the operation, the dogs were randomized to receive one of two peptides or a placebo. Injections of vascular endothelial growth hormone (VEGF) 45 µg (N=9), basic fibroblast growth factor (bFGF) 110 µg (N=9), or placebo (N-12) were made on a daily basis (Monday through Friday). Treatment was continued for a duration of four weeks. (VEGF, bFGF or placebo were injected directly into the distal LCX through the subcutaneous catheter. Solutions were given as a slow bolus (2 ml over 2 minutes) followed by 1 ml saline flush. Blood flow was quantified on a weekly basis.

EXAMPLE 2

Figure 2:
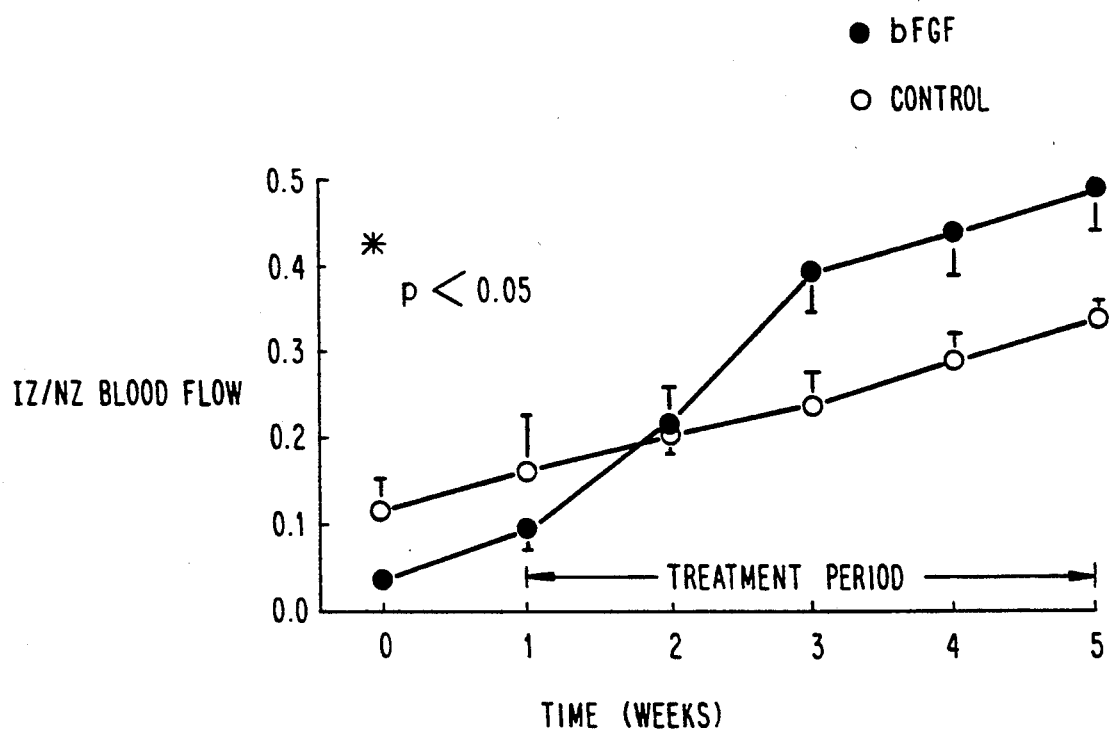
FIG. 2 is a graphical representation of the blood flow vs. time in the coronary arteries experiments with a dog's heart wherein basic fibroblast growth factor (bFGF) is injected directly into a dog's heart once daily, Monday through Friday for a 5 week period of time.

The above general procedure was followed for the intracoronary injection of basic fibroblast growth factor (bFGF). The effect of bFGF on collateral blood flow in dogs subjected to ameroid-induced occlusion of the left circumflex coronary artery (LCX). Beginning 10 days after amaroid placement, bFGF 110 micrograms (N=8) or saline (N=11) was given on a daily bolus injection directly into the LCX at a point just distal to the ameroid. Myocardial blood flow was determined with microspheres three days after ameroid placement and weekly for 5 weeks thereafter. Collateral flow was quantified during chromonar-induced maximal vasodilation and expressed as an ischemic/normal zone (IC/NZ) ratio. After two weeks of treatment the IZ/NZ ratio in bFGF treated dogs surpassed that of control dogs; final IZ/NZ blood flow ratios were $0.49 \pm 0.13$ and $0.34 \pm 0.08$ in the treated and control groups, respectively ($p < 0.05$). See FIG. 2.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of a disclosed embodiment. It is to be understood that the phraseology or terminology employed herein is for the purposes of description only and not of limitation.

We claim:

1. A method to facilitate in a damaged heart or a heart in need of improved circulation the growth of cardiac blood vessels while reducing the risk of undesired vascularization in other areas of the body comprising:
   (a) inserting a catheter into a coronary artery and providing an infusion port of said catheter accessible to the administration of coronary drug injections;
   (b) injecting an effective amount into the heart of a blood vessel growth promoting peptide through said infusion port of said catheter; and
   (c) repeating periodically on subsequent days for about 2 to 8 weeks the step of injecting said blood vessel growth promoting peptide via said catheter, with said periodic injections being continued until improved cardiac blood flow has been obtained.

2. A method according to claim 1, wherein the growth promoting peptide is selected from the group consisting of vascular endothelial growth factor, a basic fibroblast growth factor, a growth promoting bioactive peptide fragment of vascular endothelial growth factor, a growth promoting bioactive peptide fragment of basic fibroblast growth factor, or a mixture of said peptides.

3. A method according to claim 1, wherein said growth promoting peptide is in the form of a solution, which is administered, over a period of 10 seconds to about 10 hours.

4. A method according to claim 1, wherein said growth promoting peptide is in the form of a solution, which is administered as a slow bolus, which comprises about two ml of the solution comprising said growth promoting peptide, over a two minute period of time followed by a one ml saline flush.

5. A method according to claim 1, wherein the growth promoting peptide is administered continuously over hours or days at such a rate as to obtain the desired daily effective dosage amount.

6. A method according to claim 2, wherein the said peptide is vascular endothelial growth factor, which is administered in an amount of about 200–500 μg per injection.

7. A method according to claim 6, wherein said vascular endothelial growth factor is administered in an amount of about 25–200 μg per injection.

8. A method according to claim 6, wherein the vascular endothelial growth factor is injected at about 45 μg per injection, which injection is made once per day on the days that injections are administered.

9. A method according to claim 2, wherein the basic fibroblast growth factor is administered in an amount of about 50–700 μg per injection.

10. A method according to claim 9, wherein the basic fibroblast growth factor is administered in an amount of about 75–300 μg per injection.

11. A method according to claim 9, further comprising injecting about 110 μg of vascular basic fibroblast growth factor per injection, which injection is made once per day on the days that injections are administered.

12. A method according to claim 1 further comprising the step of determining the rate and sufficiency of miocardia blood flow by microspheres after the placement of the catheter and prior to treatment; and subsequently determining the rate and sufficiency of blood flow on a weekly basis during the course of treatment.

13. A method according to claim 12, wherein the collateral myocardial blood flow can be quantified during chromonar-induced maximum vasal dilation and expressed as an ischemic/normal zone ratio represented by the formula ratio IZ/NZ.

* * * * *